United States Patent
Bundock

(10) Patent No.: US 12,331,309 B2
(45) Date of Patent: Jun. 17, 2025

(54) METHOD FOR TARGETED ALTERATION OF DUPLEX DNA

(71) Applicant: Keygene N.V., Wageningen (NL)

(72) Inventor: Paul Bundock, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 16/449,326

(22) Filed: Jun. 21, 2019

(65) Prior Publication Data

US 2020/0080110 A1  Mar. 12, 2020

Related U.S. Application Data

(63) Continuation of application No. PCT/EP2017/084293, filed on Dec. 22, 2017.

(51) Int. Cl.
| | |
|---|---|
| C12N 15/90 | (2006.01) |
| C12N 9/22 | (2006.01) |
| C12N 15/10 | (2006.01) |
| C12N 15/11 | (2006.01) |

(52) U.S. Cl.
CPC ............... *C12N 15/90* (2013.01); *C12N 9/22* (2013.01); *C12N 15/102* (2013.01); *C12N 15/11* (2013.01); *C12N 2310/20* (2017.05); *C12N 2800/80* (2013.01)

(58) Field of Classification Search
CPC ..................................................... C12N 15/90
USPC ......................................................... 435/468
See application file for complete search history.

(56) References Cited

U.S. PATENT DOCUMENTS

| | | | |
|---|---|---|---|
| 6,262,338 B1 | 7/2001 | Schreier et al. | |
| 2013/0326725 A1* | 12/2013 | Shukla ................. | C12Y 301/00 800/278 |
| 2016/0208243 A1* | 7/2016 | Zhang .................... | C12N 15/10 |
| 2018/0044700 A1* | 2/2018 | Doudna .................. | C12P 19/34 |

FOREIGN PATENT DOCUMENTS

| | | |
|---|---|---|
| EP | 3 009 511 A2 | 4/2016 |
| WO | WO-2015/139008 A1 | 9/2015 |
| WO | 2016201138 | 12/2016 |
| WO | 2017/218185 A1 | 12/2017 |
| WO | 2018/099475 A1 | 6/2018 |

OTHER PUBLICATIONS

Malnoy et al. Frontiers in Plant Science 7:1-9 (Year: 2016).*
Gao et al. "Type V CRISPR-Cas Cpf1 endonuclease employs a unique mechanism for crRNA-mediated target DNA recognition." Cell research 26.8 (2016): 901-913.
International Search Report mailed Apr. 19, 2018 for International Patent Application No. PCT/EP2017/084293 filed Dec. 22, 2017. 5 pages.
Ma et al. "CRISPR/Cas9 platforms for genome editing in plants: developments and applications." Molecular plant 9.7 (2016): 961-974.
Schiml et al. "Revolutionizing plant biology: multiple ways of genome engineering by CRISPR/Cas." Plant methods 12.1 (2016): 8.
Zetsche et al., "Cpf1 is a single RNA-guided endonuclease of a class 2 CRISPR-Cas system", Cell, Oct. 1, 2015, vol. 163, No. 3, pp. 759-771.
Maas C. and Werr W., "Mechanism and optimized conditions for PEG mediated DNA transfection into plant protoplasts", Plant Cell Reports (1989) 8:148-151.
Zhou et al., "Exploiting SNPs for biallelic CRISPR mutations in the outcrossing woody perennial Populus reveals 4-coumarate: CoA ligase specificity and redundancy" New Phytologist, (2015), 208: 298-301.
Lowder L., "Rapid Evolution in Manifold CRISPR Systems for Plnt Genome Editing" Frontiers in Plant Science, Nov. 2016, vol. 7, pp. 1-12.
Office Action issued Jan. 12, 2022 in connection with Japanese Application No. 2019-528752.
Gallie D.R., "Introduction of mRNA to plant protoplasts using polyethylene glycol" Plant Cell Reports, (1993), vol. 13, pp. 119-122.
Woo J.W., et al., "DNA-free genome editing in plants with preassembled CRISPR-Cas9 ribonucleoproteins" Nature Biotechnology, (2015), vol. 33, No. 11, pp. 1162-1165.

* cited by examiner

*Primary Examiner* — Li Zheng
(74) *Attorney, Agent, or Firm* — Troutman Pepper Locke LLP

(57) ABSTRACT

The current invention relates to methods of targeted genetic alteration in plant cells, as well as to plant cells and plants thus obtained. In the method, a Cpf1 protein and a crRNA is employed to provide for targeted alteration, in particular increased biallelic alteration, of a DNA duplex with increased efficacy.

13 Claims, 6 Drawing Sheets

Specification includes a Sequence Listing.

Fig. 1.1

Protein sequence of Cpf1-His-NLS (SEQ ID NO:7)

MTQFEGFTNLYQVSKTLRFELIPQGKTLKHIQEQGFIEEDKARNDHYKELKPIIDRIYKTYADQCLQLVQ
LDWENLSAAIDSYRKEKTEETRNALIEEQATYRNAIHDYFIGRTDNLTDAINKRHAEIYKGLFKAELFNG
KVLKQLGTVTTTEHENALLRSFDKFTTYFSGFYENRKNVFSAEDISTAIPHRIVQDNFPKFKENCHIFTR
LITAVPSLREHFENVKKAIGIFVSTSIEEVFSFPFYNQLLTQTQIDLYNQLLGGISREAGTEKIKGLNEV
LNLAIQKNDETAHIIASLPHRFIPLFKQILSDRNTLSFILEEFKSDEEVIQSFCKYKTLLRNENVLETAE
ALFNELNSIDLTHIFISHKKLETISSALCDHWDTLRNALYERRISELTGKITKSAKEKVQRSLKHEDINL
QEIISAAGKELSEAFKQKTSEILSHAHAALDQPLPTTLKKQEEKEILKSQLDSLLGLYHLLDWFAVDESN
EVDPEFSARLTGIKLEMEPSLSFYNKARNYATKKPYSVEKFKLNFQMPTLASGWDVNKEKNNGAILFVKN
GLYYLGIMPKQKGRYKALSFEPTEKTSEGFDKMYYDYFPDAAKMIPKCSTQLKAVTAHFQTHTTPILLSN
NFIEPLEITKEIYDLNNPEKEPKKFQTAYAKKTGDQKGYREALCKWIDFTRDFLSKYTKTTSIDLSSLRP
SSQYKDLGEYYAELNPLLYHISFQRIAEKEIMDAVETGKLYLFQIYNKDFAKGHHGKPNLHTLYWTGLFS
PENLAKTSIKLNGQAELFYRPKSRMKRMAHRLGEKMLNKKLKDQKTPIPDTLYQELYDYVNHRLSHDLSD
EARALLPNVITKEVSHEIIKDRRFTSDKFFFHVPITLNYQAANSPSKFNQRVNAYLKEHPETPIIGIDRG
ERNLIYITVIDSTGKILEQRSLNTIQQFDYQKKLDNREKERVAARQAWSVVGTIKDLKQGYLSQVIHEIV
DLMIHYQAVVVLENLNFGFKSKRTGIAEKAVYQQFEKMLIDKLNCLVLKDYPAEKVGGVLNPYQLTDQFT
SFAKMGTQSGFLFYVPAPYTSKIDPLTGFVDPFVWKTIKNHESRKHFLEGFDFLHYDVKTGDFILHFKMN
RNLSFQRGLPGFMPAWDIVFEKNETQFDAKGTPFIAGKRIVPVIENHRFTGRYRDLYPANELIALLEEKG
IVFRDGSNILPKLLENDDSHAIDTMVALIRSVLQMRNSNAATGEDYINSPVRDLNGVCFDSRFQNPEWPM
DADANGAYHIALKGQLLLNHLKESKDLKLQNGISNQDWLAYIQELRNGRGS<u>HHHHHHKLP</u>KKKRKV\*

Nucleotide sequence of the Cpf1-His-NLS ORF (SEQ ID NO:8)

ATGACTCAGTTCGAGGGATTCACTAACCTTTACCAGGTGTCAAAGACTCTTAGGTTCGAGCTTATCCCAC
AGGGAAAGACTTTGAAGCACATCCAAGAGCAGGGATTCATCGAAGAGGATAAGGCTAGGAACGATCACTA
CAAAGAGCTTAAGCCAATCATCGATAGGATCTACAAGACTTACGCTGATCAGTGCCTTCAGCTTGTGCAG
CTTGATTGGGAGAACCTTTCTGCTGCTATCGATTCTTATAGGAAGAAAAGACTGAAGAGACTAGGAACG
CTCTTATCGAGGAACAGGCTACTTACAGAAACGCTATCCACGATTACTTCATCGGAAGGACTGATAACTT
GACTGATGCTATCAACAAGAGGCACGCTGAGATCTATAAGGGACTTTTCAAGGCTGAGCTTTTCAACGGA
AAGGTGTTGAAGCAGCTTGGAACTGTGACTACTACTGAGCACGAGAACGCTTTGCTTAGATCTTTCGATA
AGTTCACTACTTACTTCTCTGGATTCTACGAGAACAGAAAGAACGTGTTCTCTGCTGAGGATATCTCTAC
TGCTATCCCACACAGGATCGTGCAGGATAACTTCCCAAAGTTCAAAGAGAACTGCCACATCTTCACTAGG
CTTATCACTGCTGTGCCATCTCTTAGGGAACACTTCGAGAACGTGAAGAAGGCTATCGGAATCTTCGTGT
CTACTTCAATCGAGGAAGTGTTCTCTTTTCCCTTTCTACAATCAACTTCTTACTCAGACTCAGATTGATCT
TTACAACCAGCTTCTTGGAGGAATCTCAAGAGAGGCTGGAACTGAGAAGATCAAGGGACTTAACGAGGTT
TTGAACCTTGCTATCCAAAAGAACGATGAGACTGCTCACATTATCGCTTCACTTCCACACAGATTCATCC
CTTTGTTCAAGCAGATCCTTTCTGATAGGAACACTTTGTCTTTCATCCTTGAAGAGTTCAAGTCTGATGA
AGAGGTGATCCAGTCTTTCTGCAAGTACAAGACTCTTCTTAGGAACGAGAATGTGTTGGAGACTGCTGAG
GCTCTTTTCAATGAGCTTAACTCTATCGATCTTACTCACATTTTCATCTCTCACAAGAAGCTTGAGACTA
TCTCTTCTGCTCTTTGCGATCACTGGGATACTTTGAGGAACGCACTTTACGAGAGAAGGATCTCTGAGCT
TACTGGAAAGATCACTAAGTCTGCTAAAGAGAAGGTTCAGAGATCACTTAAGCACGAGGATATCAACCTT
CAAGAGATCATCTCTGCTGCTGGAAAAGAGCTTTCTGAGGCTTTCAAGCAAAAGACTTCTGAGATCTTGT
CTCACGCTCACGCTGCTCTTGATCAGCCACTTCCAACTACTCTTAAGAAGCAAGAAGAGAAAGAGATCTT
GAAGTCTCAGTTGGATTCTCTTTTGGGACTTTACCACCTTCTTGATTGGTTCGCTGTGGATGAGTCTAAC

 

Fig. 1.2

```
GAAGTGGATCCAGAGTTCTCAGCTAGGTTGACTGGAATCAAGTTGGAGATGGAACCATCTCTTTCATTCT
ACAACAAGGCTAGAAACTACGCTACTAAGAAGCCATACTCTGTTGAGAAGTTCAAGCTTAATTTCCAGAT
GCCAACTTTGGCTTCTGGATGGGATGTGAACAAAGAAAAAAACAACGGTGCTATCCTTTTCGTGAAGAAC
GGACTTTACTACTTGGGAATCATGCCAAAGCAGAAGGGAAGGTACAAGGCTTTGTCATTCGAGCCAACTG
AAAAGACATCAGAGGGATTCGATAAGATGTACTATGATTACTTCCCAGATGCTGCTAAGATGATCCCAAA
GTGCTCTACTCAGCTTAAGGCTGTGACAGCTCACTTCCAGACTCACACTACTCCAATCCTTTTGTCTAAC
AACTTCATCGAGCCACTTGAGATCACAAAAGAAATCTACGATCTTAACAACCCTGAGAAAGAGCCAAAAA
AGTTCCAGACTGCTTACGCTAAAAAGACTGGTGATCAGAAGGGATACAGGGAAGCTTTGTGCAAGTGGAT
CGATTTTACTAGGGATTTCTTGTCTAAGTACACTAAGACTACTTCTATCGATTTGTCATCTTTGAGGCCA
TCTTCACAGTACAAGGATCTTGGAGAGTACTACGCTGAGTTGAACCCACTTCTTTACCACATCTCATTCC
AGAGGATCGCAGAGAAAGAAATCATGGATGCTGTTGAGACTGGAAAGCTTTACCTTTTCCAAATCTATAA
CAAGGATTTCGCTAAGGGACACCACGGAAAGCCAAACCTTCACACTCTTTACTGGACTGGACTTTTCTCA
CCAGAGAACTTGGCTAAGACTTCTATCAAGTTGAACGGACAGGCTGAGTTGTTCTACAGGCCAAAGTCTA
GGATGAAGAGAATGGCTCACAGGCTTGGAGAGAAGATGCTTAACAAAAGTTGAAGGATCAAAAGACTCC
TATCCCAGATACTCTTTACCAAGAGCTTTACGATTACGTGAACCACAGGCTTTCTCACGATCTTTCTGAT
GAGGCTAGGGCTCTTTTGCCAAACGTTATCACAAAAGAGGTGTCACACGAGATCATCAAGGATAGAAGGT
TTACTTCTGATAAGTTCTTCTTCCACGTGCCAATCACTCTTAACTACCAGGCTGCTAACTCTCCATCTAA
GTTCAACCAGAGGGTGAACGCTTACCTTAAAGAGCACCCAGAGACACCTATCATCGGTATCGATAGGGGA
GAGAGGAACCTTATCTACATCACTGTGATCGATTCTACTGGTAAGATTCTTGAGCAGAGATCTTTGAACA
CTATCCAGCAGTTCGATTACCAGAAGAAGTTGGATAACAGGGAAAAAGAGAGGGTTGCAGCTAGGCAGGC
TTGGTCTGTTGTGGGAACTATCAAGGATTTGAAGCAGGGATACTTGTCTCAGGTTATCCACGAGATTGTG
GATTTGATGATCCACTACCAAGCTGTGGTGGTGCTTGAGAACCTTAACTTCGGATTCAAGTCTAAGAGGA
CTGGTATCGCTGAGAAGGCTGTGTACCAACAGTTCGAGAAGATGTTGATCGATAAGCTTAACTGCCTTGT
GCTTAAGGATTACCCTGCTGAAAAGGTGGGAGGTGTGCTTAACCCATACCAGCTTACAGATCAGTTCACT
TCATTCGCTAAGATGGGAACTCAGTCTGGTTTCTTGTTCTACGTTCCAGCTCCATACACATCAAAGATCG
ATCCATTGACTGGATTCGTGGATCCTTTCGTGTGGAAAACTATTAAGAACCACGAGTCTAGGAAGCACTT
CCTTGAGGGTTTCGATTTCCTTCACTACGATGTGAAAACTGGTGATTTCATCTTGCACTTTAAGATGAAT
AGGAACTTGTCTTTCCAGAGGGGTTTGCCAGGATTCATGCCAGCTTGGGATATCGTGTTTGAGAAGAACG
AGACACAGTTCGATGCTAAGGGAACTCCATTCATTGCTGGTAAGAGGATTGTGCCAGTGATTGAGAACCA
TAGGTTCACTGGTAGGTACAGGGATCTTTACCCAGCTAACGAGTTGATCGCTTTGTTGGAAGAGAAGGGA
ATCGTGTTCAGGGATGGATCTAATATCCTTCCAAAGCTTTTGGAGAATGATGATTCTCACGCAATCGATA
CAATGGTGGCTCTTATCAGATCTGTGCTTCAGATGAGGAACTCTAACGCTGCTACTGGTGAGGATTACAT
CAACTCTCCAGTGAGGGATCTTAACGGTGTGTGCTTCGATTCTAGGTTCCAGAATCCTGAGTGGCCAATG
GATGCAGATGCTAACGGTGCTTACCACATTGCTCTTAAGGGACAGCTTCTTCTTAACCACTTGAAAGAGT
CTAAGGATCTTAAGCTTCAGAACGGAATCTCTAACCAGGATTGGCTTGCTTACATTCAAGAGCTTAGGAA
TGGAAGGGGATCTCATCACCACCACCATCACAAGCTTCCAAAAAAGAAGAGGAAGGTTTAG
```

Fig. 2 crRNA1 PDS1 (SEQ ID NO:9)

GGAGTGATCAAAAGTCCCACATCGATCAGGTGATATATAGCAGCTTAGTTTATATAATGATAGAGTCGAC
ATAGCGATT*TAATTTCTACTCTTGTAGAT*AGTTCCCAAAGAAGACGACCTCGAGCTCTAGACCCAGCTTT
CTTGTACAAAGTTGGCATTACGCT crRNA2 PDS1 (SEQ ID NO:10)

GGAGTGATCAAAAGTCCCACATCGATCAGGTGATATATAGCAGCTTAGTTTATATAATGATAGAGTCGAC
ATAGCGATT*TAATTTCTACTCTTGTAGAT*ACTTCTGAGGTTTGTGGATCTTTCTAGACCCAGCTTTCTTG
TACAAAGTTGGCATTACGCT sgRNA PDS1 (SEQ ID NO:11)

GGAGTGATCAAAAGTCCCACATCGATCAGGTGATATATAGCAGCTTAGTTTATATAATGATAGAGTCGAC
ATAGCGATTGAGCTCGAGGTCGTCTTCTTT*GTTTTAGAGCTAGAAATAGCAAGTTAAAATAAGGCTAGTC
CGTTATCAACTTGAAAAAGTGGCACCGAGTCGGTGCTTTTTTT*CTAGACCCAGCTTTCTTGTACAAAGTT
GGCATTACGCT crRNA MET1 (SEQ ID NO:12)

GGAGTGATCAAAAGTCCCACATCGATCAGGTGATATATAGCAGCTTAGTTTATATAATGATAGAGTCGAC
ATAGCGATT*TAATTTCTACTCTTGTAGAT*AAATCTGAACAGGCAGCAGCTCGCTTCTAGACCCAGCTTTC
TTGTACAAAGTTGGCATTACGCT sgRNA Met1 (SEQ ID NO:13)

GGAGTGATCAAAAGTCCCACATCGATCAGGTGATATATAGCAGCTTAGTTTATATAATGATAGAGTCGAC
ATAGCGATTGTCTGAACAGGCAGCAGCTCGCTT*GTTTTAGAGCTAGAAATAGCAAGTTAAAATAAGGCTA
GTCCGTTATCAACTTGAAAAAGTGGCACCGAGTCGGTGCTTTTTTT*CTAGACCCAGCTTTCTTGTACAAA
GTTGGCATTACGCT crRNA 3g095310 (SEQ ID NO:14)

GGAGTGATCAAAAGTCCCACATCGATCAGGTGATATATAGCAGCTTAGTTTATATAATGATAGAGTCGAC
ATAGCGATT*TAATTTCTACTCTTGTAGAT* CTCACGGATACGAGATTGCCATTCCTAGACCCAGCTTTCTT

GTACAAAGTTGGCATTACGCT sgRNA 3g095310 (SEQ ID NO:15)

GGAGTGATCAAAAGTCCCACATCGATCAGGTGATATATAGCAGCTTAGTTTATATAATGATAGAGTCGAC
ATAGCGATTGCGGATACGAGATTGCCATTC*GTTTTAGAGCTAGAAATAGCAAGTTAAAATAAGGCTAGTC

CGTTATCAACTTGAAAAAGTGGCACCGAGTCGGTGCTTTTTTT*CTAGACCCAGCTTTCTTGTACAAAGTT
GGCATTACGCT

Fig. 4

CATCTCGACTTTC<u>*AGTTCCCAAAGAAGACGACCTCGAGCT*</u>CCAAAGATAAGCTGAACT crRNA1 target (SEQ ID NO:16)

CATCTCGACTTTC*AGTTCCCAAAGA*------*CCTCGAGCT*CCAAAGATAAGCTGAACT (SEQ ID NO:17)

CATCTCGACTTTC*AGTTCCCAAAGAA*---------*GAGCT*CCAAAGATAAGCTGAACT (SEQ ID NO:18)

CATCTCGACTTTC*AGTTCCCAAAGAAG*------*TCGAGCT*CCAAAGATAAGCTGAACT (SEQ ID NO:19)

CATCTCGACTTTC*AGTTCCCAAAGAA*----------*AGCT*CCAAAGATAAGCTGAACT (SEQ ID NO:20)

CATCTCGACTTTC*AGTTCCCAA*--------------*AGCT*CCAAAGATAAGCTGAACT (SEQ ID NO:21)

CATCTCGACTTTCAGTTCCC<u>AAAGAAGACGACCTCGAGCTCCAAAGATAAG</u> sgRNA PDS1 (SEQ ID NO:22)

CATCTCGACTTTCAGTTCCCAAA------GACCTCGAGCTCCAAAGATAAG (SEQ ID NO:23)

CATCTCGACTTTCAGTTCCCAAA----ACGACCTCGAGCTCCAAAGATAAG (SEQ ID NO:24)

CATCTCGACTTTCAGTTCCCA---AAGACGACCTCGAGCTCCAAAGATAAG (SEQ ID NO:25)

CATCTCGACTTTCAGTTCCCAA--AAGACGACCTCGAGCTCCAAAGATAAG (SEQ ID NO:26)

CATCTCGACTTTCAGTTCCCAA-----ACGACCTCGAGCTCCAAAGATAAG (SEQ ID NO:27)

CCACTCGTTTA<u>ACTTCTGAGGTTTGTGGATCTTTTAGGCGACTTTTTTTTTT</u> crRNA2 PDS1 (SEQ ID NO:28)

CCACTCGTTTAACTTCTGAGGTTT----------TAGGCGACTTTTTTTTTT (SEQ ID NO:29)

CCACTCGTTTAACTTCTGAGGTTT------------GGCGACTTTTTTTTTT (SEQ ID NO:30)

CCACTCGTTTAACTTCTGAGGTTT---------TTAGGCGACTTTTTTTTTT (SEQ ID NO:31)

CCACTCGTTTAACTTCTGAGGTTTGT--------TAGGCGACTTTTTTTTTT (SEQ ID NO:32)

CCACTCGTTTAACTTCTGAGGTT-----------AGGCGACTTTTTTTTTT (SEQ ID NO:33)

SEQUENCE LISTING

```
<160> NUMBER OF SEQ ID NOS: 33

<210> SEQ ID NO 1
<211> LENGTH: 18
<212> TYPE: DNA
<213> ORGANISM: Artificial sequence
<220> FEATURE:
<223> OTHER INFORMATION: First primer SlPDS1

<400> SEQUENCE: 1
tgtgcagaac cactccct                                                 18

<210> SEQ ID NO 2
<211> LENGTH: 18
<212> TYPE: DNA
<213> ORGANISM: Artificial sequence
<220> FEATURE:
<223> OTHER INFORMATION: Second primer SlPDS1

<400> SEQUENCE: 2
tttagttggg cgcggaga                                                 18

<210> SEQ ID NO 3
<211> LENGTH: 21
<212> TYPE: DNA
```

```
<213> ORGANISM: Artificial sequence
<220> FEATURE:
<223> OTHER INFORMATION: Primer 1 Solyc13g095310

<400> SEQUENCE: 3
atgggaagcg gtgaaagaaa g                                      21

<210> SEQ ID NO 4
<211> LENGTH: 21
<212> TYPE: DNA
<213> ORGANISM: Artificial sequence
<220> FEATURE:
<223> OTHER INFORMATION: Primer 2 Solyc13g095310

<400> SEQUENCE: 4
agggtcacga tgaagagttg g                                      21

<210> SEQ ID NO 5
<211> LENGTH: 22
<212> TYPE: DNA
<213> ORGANISM: Artificial sequence
<220> FEATURE:
<223> OTHER INFORMATION: Primer 1 SlMET1

<400> SEQUENCE: 5
ggacacaaaa agaacaaacg ca                                     22

<210> SEQ ID NO 6
<211> LENGTH: 18
<212> TYPE: DNA
<213> ORGANISM: Artificial sequence
<220> FEATURE:
<223> OTHER INFORMATION: Primer 2 SlMET1

<400> SEQUENCE: 6
tatgaacccg ccctgagt                                          18

<210> SEQ ID NO 7
<211> LENGTH: 1326
<212> TYPE: PRT
<213> ORGANISM: Artificial sequence
<220> FEATURE:
<223> OTHER INFORMATION: Protein sequence of Cpf1-His-NLS

<400> SEQUENCE: 7
```

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys

```
                130             135             140
Gln Leu Gly Thr Val Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Glu Asn Cys His Ile Phe
                195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
                370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560
```

-continued

```
Gly Leu Tyr Tyr Leu Gly Ile Met Pro Lys Gln Lys Gly Arg Tyr Lys
                565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
        595                 600                 605
Ser Thr Gln Leu Lys Ala Val Thr Ala His Phe Gln Thr His Thr Thr
    610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                645                 650                 655
Thr Ala Tyr Ala Lys Lys Thr Gly Asp Gln Lys Gly Tyr Arg Glu Ala
            660                 665                 670
Leu Cys Lys Trp Ile Asp Phe Thr Arg Asp Phe Leu Ser Lys Tyr Thr
        675                 680                 685
Lys Thr Thr Ser Ile Asp Leu Ser Ser Leu Arg Pro Ser Ser Gln Tyr
    690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
            740                 745                 750
Gly His His Gly Lys Pro Asn Leu His Thr Leu Tyr Trp Thr Gly Leu
        755                 760                 765
Phe Ser Pro Glu Asn Leu Ala Lys Thr Ser Ile Lys Leu Asn Gly Gln
    770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
            820                 825                 830
Arg Leu Ser His Asp Leu Ser Asp Glu Ala Arg Ala Leu Leu Pro Asn
        835                 840                 845
Val Ile Thr Lys Glu Val Ser His Glu Ile Ile Lys Asp Arg Arg Phe
    850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
            900                 905                 910
Asn Leu Ile Tyr Ile Thr Val Ile Asp Ser Thr Gly Lys Ile Leu Glu
        915                 920                 925
Gln Arg Ser Leu Asn Thr Ile Gln Gln Phe Asp Tyr Gln Lys Lys Leu
    930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
```

His Glu Ile Val Asp Leu Met Ile His Tyr Gln Ala Val Val Leu
                  980             985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn Gly
    1295                1300                1305

Arg Gly Ser His His His His His His Lys Leu Pro Lys Lys Lys
    1310                1315                1320

Arg Lys Val
    1325

<210> SEQ ID NO 8
<211> LENGTH: 3981
<212> TYPE: DNA
<213> ORGANISM: Artificial sequence
<220> FEATURE:
<223> OTHER INFORMATION: Nucleotide sequence of the Cpf1-His-NLS ORF

<400> SEQUENCE: 8

```
atgactcagt tcgagggatt cactaacctt taccaggtgt caaagactct taggttcgag      60
cttatcccac agggaaagac tttgaagcac atccaagagc agggattcat cgaagaggat     120
aaggctagga acgatcacta caaagagctt aagccaatca tcgataggat ctacaagact     180
tacgctgatc agtgccttca gcttgtgcag cttgattggg agaacctttc tgctgctatc     240
gattcttata ggaaagaaaa gactgaagag actaggaacg ctcttatcga ggaacaggct     300
acttacagaa acgctatcca cgattacttc atcggaagga ctgataactt gactgatgct     360
atcaacaaga ggcacgctga gatctataag ggacttttca aggctgagct tttcaacgga     420
aaggtgttga agcagcttgg aactgtgact actactgagc acgagaacgc tttgcttaga     480
tctttcgata agttcactac ttacttctct ggattctacg agaacagaaa gaacgtgttc     540
tctgctgagg atatctctac tgctatccca cacaggatcg tgcaggataa cttcccaaag     600
ttcaaagaga actgccacat cttcactagg cttatcactg ctgtgccatc tcttagggaa     660
cacttcgaga acgtgaagaa ggctatcgga atcttcgtgt ctacttcaat cgaggaagtg     720
ttctctttcc ctttctacaa tcaacttctt actcagactc agattgatct ttacaaccag     780
cttcttggag aatctcaag agaggctgga actgagaaga tcaagggact taacgaggtt     840
ttgaaccttg ctatccaaaa gaacgatgag actgctcaca ttatcgcttc acttccacac     900
agattcatcc ctttgttcaa gcagatcctt tctgatagga cactttgtc tttcatcctt     960
gaagagttca gtctgatga agaggtgatc cagtctttct gcaagtacaa gactcttctt    1020
aggaacgaga atgtgttgga gactgctgag gctctttttca atgagcttaa ctctatcgat    1080
cttactcaca ttttcatctc tcacaagaag cttgagacta tctcttctgc tctttgcgat    1140
cactgggata ctttgaggaa cgcactttac gagagaagga tctctgagct tactggaaag    1200
atcactaagt ctgctaaaga aaggttcag agatcactta agcacgagga tatcaacctt    1260
caagagatca tctctgctgc tggaaaagag ctttctgagg ctttcaagca aaagacttct    1320
gagatcttgt ctcacgctca cgctgctctt gatcagccac ttccaactac tcttaagaag    1380
caagaagaga aagagatctt gaagtctcag ttggattctc ttttgggact ttaccacctt    1440
cttgattggt tcgctgtgga tgagtctaac gaagtggatc cagagttctc agctaggttg    1500
actggaatca agttggagat ggaaccatct ctttcattct acaacaaggc tagaaactac    1560
gctactaaga agccatactc tgttgagaag ttcaagctta atttccagat gccaactttg    1620
gcttctggat gggatgtgaa caaagaaaaa acaacggtg ctatccttt cgtgaagaac    1680
ggactttact acttgggaat catgccaaag cagaagggaa ggtacaaggc tttgtcattc    1740
gagccaactg aaaagacatc agagggattc gataagatgt actatgatta cttcccagat    1800
gctgctaaga tgatcccaaa gtgctctact cagcttaagg ctgtgacagc tcacttccag    1860
actcacacta ctccaatcct tttgtctaac aacttcatcg agccacttga gatcacaaaa    1920
gaaatctacg atcttaacaa ccctgagaaa gagccaaaaa agttccagac tgcttacgct    1980
aaaaagactg gtgatcagaa gggatacagg gaagctttgt gcaagtggat cgattttact    2040
agggatttct tgtctaagta cactaagact acttctatcg atttgtcatc tttgaggcca    2100
tcttcacagt acaaggatct tggagagtac tacgctgagt tgaacccact tctttaccac    2160
atctcattcc agaggatcgc agagaaagaa atcatggatg ctgttgagac tggaaagctt    2220
tacctttttcc aaatctataa caaggatttc gctaagggac accacggaaa gccaaacctt    2280
```

```
cacactctttt actggactgg acttttctca ccagagaact tggctaagac ttctatcaag    2340
ttgaacggac aggctgagtt gttctacagg ccaaagtcta ggatgaagag aatggctcac    2400
aggcttggag agaagatgct taacaaaaag ttgaaggatc aaaagactcc tatcccagat    2460
actctttacc aagagcttta cgattacgtg aaccacaggc tttctcacga tctttctgat    2520
gaggctaggg ctcttttgcc aaacgttatc acaaagagg tgtcacacga gatcatcaag    2580
gatagaaggt ttacttctga taagttcttc ttccacgtgc caatcactct taactaccag    2640
gctgctaact ctccatctaa gttcaaccag agggtgaacg cttaccttaa agagcaccca    2700
gagacaccta tcatcggtat cgataggga gagaggaacc ttatctacat cactgtgatc    2760
gattctactg gtaagattct tgagcagaga tctttgaaca ctatccagca gttcgattac    2820
cagaagaagt tggataacag ggaaaaagag agggttgcag ctaggcaggc ttggtctgtt    2880
gtgggaacta tcaaggattt gaagcaggga tacttgtctc aggttatcca cgagattgtg    2940
gatttgatga tccactacca agctgtggtg gtgcttgaga accttaactt cggattcaag    3000
tctaagagga ctggtatcgc tgagaaggct gtgtaccaac agttcgagaa gatgttgatc    3060
gataagctta actgccttgt gcttaaggat taccctgctg aaaaggtggg aggtgtgctt    3120
aacccatacc agcttacaga tcagttcact tcattcgcta gatgggaac tcagtctggt    3180 ttcttgttct acgttccagc tccatacaca tcaaagatcg atccattgac tggattcgtg    3240
gatcctttcg tgtggaaaac tattaagaac cacgagtcta ggaagcactt ccttgagggt    3300
ttcgatttcc ttcactacga tgtgaaaact ggtgatttca tcttgcactt taagatgaat    3360
aggaacttgt ctttccagag gggttttgcca ggattcatgc cagcttggga tatcgtgttt    3420
gagaagaacg agacacagtt cgatgctaag ggaactccat tcattgctgg taagaggatt    3480
gtgccagtga ttgagaacca taggttcact ggtaggtaca gggatcttta cccagctaac    3540
gagttgatcg ctttgttgga agagaaggga atcgtgttca gggatggatc taatatcctt    3600
ccaaagcttt tggagaatga tgattctcac gcaatcgata caatggtggc tcttatcaga    3660
tctgtgcttc agatgaggaa ctctaacgct gctactggtg aggattacat caactctcca    3720
gtgagggatc ttaacggtgt gtgcttcgat tctaggttcc agaatcctga gtggccaatg    3780
gatgcagatg ctaacggtgc ttaccacatt gctcttaagg acagcttct tcttaaccac    3840 ttgaaagagt ctaaggatct taagcttcag aacggaatct ctaaccagga ttggcttgct    3900
tacattcaag agcttaggaa tggaagggga tctcatcacc accaccatca aagcttcca    3960 aaaaagaaga ggaaggttta g                                              3981

<210> SEQ ID NO 9
<211> LENGTH: 164
<212> TYPE: DNA
<213> ORGANISM: Artificial sequence
<220> FEATURE:
<223> OTHER INFORMATION: crRNA1 PDS1

<400> SEQUENCE: 9
ggagtgatca aaagtcccac atcgatcagg tgatatatag cagcttagtt tatataatga      60
tagagtcgac atagcgattt aatttctact cttgtagata gttcccaaag aagacgacct     120
cgagctctag acccagcttt cttgtacaaa gttggcatta cgct                      164

<210> SEQ ID NO 10
<211> LENGTH: 160
<212> TYPE: DNA
<213> ORGANISM: Artificial sequence
```

<220> FEATURE:
<223> OTHER INFORMATION: crRNA2 PDS1

<400> SEQUENCE: 10

```
ggagtgatca aaagtcccac atcgatcagg tgatatatag cagcttagtt tatataatga    60
tagagtcgac atagcgattt aatttctact cttgtagata cttctgaggt ttgtggatct   120
ttctagaccc agctttcttg tacaaagttg gcattacgct                         160
```

<210> SEQ ID NO 11
<211> LENGTH: 221
<212> TYPE: DNA
<213> ORGANISM: Artificial sequence
<220> FEATURE:
<223> OTHER INFORMATION: sgRNA PDS1

<400> SEQUENCE: 11

```
ggagtgatca aaagtcccac atcgatcagg tgatatatag cagcttagtt tatataatga    60
tagagtcgac atagcgattg agctcgaggt cgtcttcttt gttttagagc tagaaatagc   120
aagttaaaat aaggctagtc cgttatcaac ttgaaaaagt ggcaccgagt cggtgctttt   180
tttctagacc cagctttctt gtacaaagtt ggcattacgc t                       221
```

<210> SEQ ID NO 12
<211> LENGTH: 163
<212> TYPE: DNA
<213> ORGANISM: Artificial sequence
<220> FEATURE:
<223> OTHER INFORMATION: crRNA MET1

<400> SEQUENCE: 12

```
ggagtgatca aaagtcccac atcgatcagg tgatatatag cagcttagtt tatataatga    60
tagagtcgac atagcgattt aatttctact cttgtagata aatctgaaca ggcagcagct   120
cgcttctaga cccagctttc ttgtacaaag ttggcattac gct                     163
```

<210> SEQ ID NO 13
<211> LENGTH: 224
<212> TYPE: DNA
<213> ORGANISM: Artificial sequence
<220> FEATURE:
<223> OTHER INFORMATION: sgRNA Met1

<400> SEQUENCE: 13

```
ggagtgatca aaagtcccac atcgatcagg tgatatatag cagcttagtt tatataatga    60
tagagtcgac atagcgattg tctgaacagg cagcagctcg cttgttttag agctagaaat   120
agcaagttaa aataaggcta gtccgttatc aacttgaaaa agtggcaccg agtcggtgct   180
ttttttctag acccagcttt cttgtacaaa gttggcatta cgct                    224
```

<210> SEQ ID NO 14
<211> LENGTH: 161
<212> TYPE: DNA
<213> ORGANISM: Artificial sequence
<220> FEATURE:
<223> OTHER INFORMATION: crRNA 3g095310

<400> SEQUENCE: 14

```
ggagtgatca aaagtcccac atcgatcagg tgatatatag cagcttagtt tatataatga    60
tagagtcgac atagcgattt aatttctact cttgtagatc tcacggatac gagattgcca   120
ttcctagacc cagctttctt gtacaaagtt ggcattacgc t                       161
```

<210> SEQ ID NO 15
<211> LENGTH: 221
<212> TYPE: DNA
<213> ORGANISM: Artificial sequence
<220> FEATURE:
<223> OTHER INFORMATION: sgRNA 3g095310

<400> SEQUENCE: 15

```
ggagtgatca aaagtcccac atcgatcagg tgatatatag cagcttagtt tatataatga      60
tagagtcgac atagcgattg cggatacgag attgccattc gttttagagc tagaaatagc     120
aagttaaaat aaggctagtc cgttatcaac ttgaaaaagt ggcaccgagt cggtgctttt     180
tttctagacc cagctttctt gtacaaagtt ggcattacgc t                         221
```

<210> SEQ ID NO 16
<211> LENGTH: 58
<212> TYPE: DNA
<213> ORGANISM: Artificial sequence
<220> FEATURE:
<223> OTHER INFORMATION: crRNA1 target

<400> SEQUENCE: 16

```
catctcgact tcagttccc aaagaagacg acctcgagct ccaaagataa gctgaact        58
```

<210> SEQ ID NO 17
<211> LENGTH: 52
<212> TYPE: DNA
<213> ORGANISM: Artificial sequence
<220> FEATURE:
<223> OTHER INFORMATION: Indel mutation generated by the Cpf1/crRNA1
      PDS1

<400> SEQUENCE: 17

```
catctcgact tcagttccc aaagacctcg agctccaaag ataagctgaa ct              52
```

<210> SEQ ID NO 18
<211> LENGTH: 49
<212> TYPE: DNA
<213> ORGANISM: Artificial sequence
<220> FEATURE:
<223> OTHER INFORMATION: Indel mutation 2 generated by the Cpf1/crRNA1
      PDS1

<400> SEQUENCE: 18

```
catctcgact tcagttccc aaagaagagc tccaaagata agctgaact                  49
```

<210> SEQ ID NO 19
<211> LENGTH: 52
<212> TYPE: DNA
<213> ORGANISM: Artificial sequence
<220> FEATURE:
<223> OTHER INFORMATION: Indel mutation 3 generated by the Cpf1/crRNA1
      PDS1

<400> SEQUENCE: 19

```
catctcgact tcagttccc aaagaagtcg agctccaaag ataagctgaa ct              52
```

<210> SEQ ID NO 20
<211> LENGTH: 48
<212> TYPE: DNA
<213> ORGANISM: Artificial sequence
<220> FEATURE:
<223> OTHER INFORMATION: Indel mutation 4 generated by the Cpf1/crRNA1
      PDS1

<400> SEQUENCE: 20
catctcgact ttcagttccc aaagaaagct ccaaagataa gctgaact      48

<210> SEQ ID NO 21
<211> LENGTH: 44
<212> TYPE: DNA
<213> ORGANISM: Artificial sequence
<220> FEATURE:
<223> OTHER INFORMATION: Indel mutation 5 generated by the Cpf1/crRNA1
      PDS1

<400> SEQUENCE: 21
catctcgact ttcagttccc aaagctccaa agataagctg aact      44

<210> SEQ ID NO 22
<211> LENGTH: 51
<212> TYPE: DNA
<213> ORGANISM: Artificial sequence
<220> FEATURE:
<223> OTHER INFORMATION: sgRNA PDS1

<400> SEQUENCE: 22
catctcgact ttcagttccc aaagaagacg acctcgagct ccaaagataa g      51

<210> SEQ ID NO 23
<211> LENGTH: 45
<212> TYPE: DNA
<213> ORGANISM: Artificial sequence
<220> FEATURE:
<223> OTHER INFORMATION: Mutation 1 generated by Cas9/sgRNA PDS1

<400> SEQUENCE: 23
catctcgact ttcagttccc aaagacctcg agctccaaag ataag      45

<210> SEQ ID NO 24
<211> LENGTH: 47
<212> TYPE: DNA
<213> ORGANISM: Artificial sequence
<220> FEATURE:
<223> OTHER INFORMATION: Mutation 2 generated by Cas9/sgRNA PDS1

<400> SEQUENCE: 24
catctcgact ttcagttccc aaaacgacct cgagctccaa agataag      47

<210> SEQ ID NO 25
<211> LENGTH: 48
<212> TYPE: DNA
<213> ORGANISM: Artificial sequence
<220> FEATURE:
<223> OTHER INFORMATION: Mutation 3 generated by the Cas9/sgRNA PDS1

<400> SEQUENCE: 25
catctcgact ttcagttccc aaagacgacc tcgagctcca agataag      48

<210> SEQ ID NO 26
<211> LENGTH: 49
<212> TYPE: DNA
<213> ORGANISM: Artificial sequence
<220> FEATURE:
<223> OTHER INFORMATION: Mutation 4 generated by the Cas9/sgRNA PDS1

<400> SEQUENCE: 26
catctcgact ttcagttccc aaaagacgac ctcgagctcc aaagataag      49

<210> SEQ ID NO 27
<211> LENGTH: 46

```
<212> TYPE: DNA
<213> ORGANISM: Artificial sequence
<220> FEATURE:
<223> OTHER INFORMATION: Mutation 5 generated by the Cas9/sgRNA PDS1

<400> SEQUENCE: 27
catctcgact ttcagttccc aaacgacctc gagctccaaa gataag          46

<210> SEQ ID NO 28
<211> LENGTH: 53
<212> TYPE: DNA
<213> ORGANISM: Artificial sequence
<220> FEATURE:
<223> OTHER INFORMATION: crRNA2 PDS1

<400> SEQUENCE: 28
ccactcgttt aacttctgag gtttgtggat cttttaggcg acttttttt ttt    53

<210> SEQ ID NO 29
<211> LENGTH: 43
<212> TYPE: DNA
<213> ORGANISM: Artificial sequence
<220> FEATURE:
<223> OTHER INFORMATION: Indel mutation 1 generated by the Cpf1/crRNA2
      PDS1

<400> SEQUENCE: 29
ccactcgttt aacttctgag gttttaggcg acttttttt ttt              43

<210> SEQ ID NO 30
<211> LENGTH: 41
<212> TYPE: DNA
<213> ORGANISM: Artificial sequence
<220> FEATURE:
<223> OTHER INFORMATION: Indel mutation 2 generated by the Cpf1/crRNA2
      PDS1

<400> SEQUENCE: 30
ccactcgttt aacttctgag gtttggcgac ttttttttt t                41

<210> SEQ ID NO 31
<211> LENGTH: 44
<212> TYPE: DNA
<213> ORGANISM: Artificial sequence
<220> FEATURE:
<223> OTHER INFORMATION: Indel mutation 3 generated by the Cpf1/crRNA2
      PDS1

<400> SEQUENCE: 31
ccactcgttt aacttctgag gttttttaggc gactttttt tttt            44

<210> SEQ ID NO 32
<211> LENGTH: 45
<212> TYPE: DNA
<213> ORGANISM: Artificial sequence
<220> FEATURE:
<223> OTHER INFORMATION: Indel mutation 4 generated by the Cpf1/crRNA2
      PDS1

<400> SEQUENCE: 32
ccactcgttt aacttctgag gtttgttagg cgactttttt ttttt           45

<210> SEQ ID NO 33
<211> LENGTH: 41
<212> TYPE: DNA
<213> ORGANISM: Artificial sequence
<220> FEATURE:
```

```
<223> OTHER INFORMATION: Indel mutation 5 generated by the Cpf1/crRNA2
      PDS1

<400> SEQUENCE: 33
ccactcgttt aacttctgag gttaggcgac ttttttttt t                    41
```

METHOD FOR TARGETED ALTERATION OF DUPLEX DNA

CROSS-REFERENCE TO RELATED PATENT APPLICATIONS

This application is a continuation of International Patent Application No. PCT/EP2017/084293, filed Dec. 22, 2017, which claims the benefit of and priority to Netherlands Application No. 2018049, filed Dec. 22, 2016. The entire disclosure of each application is incorporated by reference herein.

FIELD OF THE INVENTION

The invention relates to the field of genome or gene editing tools.

BACKGROUND OF THE INVENTION

The process of deliberately creating alterations in the genetic material of living cells generally has the goal of modifying one or more genetically encoded biological properties of that cell, or of the organism of which the cell forms part or into which it can regenerate. These changes can take the form of deletion of parts of the genetic material, addition of exogenous genetic material, or changes in the existing nucleotide sequence of the genetic material.

Methods of altering the genetic material of eukaryotic organisms have been known for over 20 years, and have found widespread application in plant, human and animal cells and micro-organisms for improvements in the fields of agriculture, human health, food quality and environmental protection.

The most common methods consist of adding exogenous DNA fragments to the genome of a cell, which will then confer a new property to that cell or its organism over and above the properties encoded by already existing genes (including applications in which the expression of existing genes will thereby be suppressed). Although many such examples are effective in obtaining the desired properties, these methods are nevertheless not very precise, because there is no control over the genomic positions in which the exogenous DNA fragments may be inserted (and hence over the ultimate levels of expression), and because the desired effect will have to manifest itself over the natural properties encoded by the original and well-balanced genome.

On the contrary, methods of genome editing that will result in the addition, deletion or conversion of nucleotides in predefined, i.e. targeted, genomic loci will allow the precise modification of the genome, for example in existing genes.

A large part of targeted genome editing described in the literature has been performed using zinc finger nucleases (ZFNs). ZFNs have been used to modify endogenous genes in a wide range of organisms and cell types. Several types of genomic alterations can be introduced with ZFNs including point mutations, deletions, insertions, inversions, duplications, and translocations, thus providing researchers with unprecedented tools to perform genetic manipulations.

In the more recent years, transcription activator-like effector nucleases (TALENs) have rapidly emerged as an alternative to ZFNs for genome editing and introducing targeted double-strand breaks (DSBs), i.e. in which both strands of the DNA duplex are severed. TALENs are similar to ZFNs and comprise a non-specific FokI nuclease domain fused to a customizable DNA-binding domain. This DNA-binding domain is composed of highly conserved repeats derived from transcription activator-like effectors (TALEs), which are proteins secreted by *Xanthomonas* bacteria to alter transcription of genes in host plant cells.

In more detail, TALEs consist of a number of repeating protein domains, each of which is able to specifically recognize and bind to one of the 4 DNA nucleotides (A,T,G,C). The domains specific for each nucleotide have been identified and arrays of these domains which have high binding affinity for any DNA sequence can be produced (Christian, 2010, Genetics 186: 757-761; Cermak et al., 2011, Nucleic Acids Res 39:e82; Bogdanove and Voytas, 2011, Science 333: 1843-1846; Boch, 2011, Nature Biotechnology 29:135-136). These arrays are then fused to the nuclease domain of FokI to create a TALEN and, similar to ZFN, two TALEN proteins are used to induce a DNA DSB in the target DNA duplex. Several papers have described the use of TALENs to create mutations at the target sequence (Curtin (2012) The Plant Genome, 5, 42-50). Joung et al. (Nat Rev Mol Cell Biol. (2013) 14(1): 49-55. doi: 10.1038/nrm3486A) reviewed and compared various techniques employing TALENs in targeted genome editing.

Recently, another novel method for targeted genome editing has been reported. CRISPRs (Clustered Regularly Interspaced Short Palindromic Repeats) are loci containing multiple short direct repeats and are found in 40% of the sequenced bacteria and 90% of sequenced archaea.

The CRISPR repeats form a system of acquired bacterial immunity against genetic pathogens such as bacteriophages and plasmids. When a bacterium is challenged with a pathogen, a small piece of the pathogen genome is processed by CRISPR associated proteins (Cas) and incorporated into the bacterial genome between CRISPR repeats. The CRISPR loci are then transcribed and processed to form so called crRNA's which include approximately 30 nucleotides of sequence identical to the pathogen genome. These RNA molecules form the basis for the recognition of the pathogen upon a subsequent infection and lead to silencing of the pathogen genetic elements through either a RNAi-like process or direct digestion of the pathogen genome.

The CRISPR-Cas systems of bacterial and archaeal adaptive immunity show extreme diversity of protein composition and genomic loci architecture. The CRISPR-Cas system has more than 50 gene families and there are no strictly universal genes indicating fast evolution and extreme diversity of loci architecture. The Cas9 protein is an example of a Cas protein of the type II CRISPR/Cas system and forms an endonuclease, when combined with the crRNA and a second RNA termed the trans-activating crRNA (tracrRNA), which targets the invading pathogen DNA for degradation by the introduction of DNA double strand breaks (DSBs) at the position in the pathogen genome defined by the crRNA. Jinek et al. (2012, Science 337: 816-820) demonstrated that a single chain chimeric guide RNA (herein *sgRNA) produced by fusing an essential portion of the crRNA and tracrRNA was able to form a function endonuclease in combination with the Cas protein.

Next to the CRISPR/CAS9 system, a new CRISPR/CAS system has recently been described, the Clustered Regularly Interspaced Short Palindromic Repeats from *Prevotella* and *Francisella* 1 or CRISPR/Cpf1. Cpf1 genes are associated with the CRISPR locus and encode an endonuclease that uses a crRNA to target DNA. Cpf1 is a smaller and simpler endonuclease than Cas9, which may overcome some of the CRISPR/Cas9 system limitations. Cpf1 is a single RNA-guided endonuclease lacking tracrRNA, and it utilizes a T-rich protospacer-adjacent motif. Cpf1 cleaves DNA via a staggered DNA double-stranded break (Zetsche et al (2015) Cell 163 (3): 759-771).

Despite these recent advances in understanding mechanisms of targeted DNA alteration, targeted alteration in plant material is still not always successful or efficient. Indeed, available methodology is often optimized for animal, in particular human, cell material and is not always successful or efficient when applied specifically to plant cells. Additionally, the prior art methodology provides genetically manipulated organisms, which, in some embodiments, is not preferred in the plant field. Thus, there is a need for new methods of providing plant cells wherein a targeted alteration has been introduced with a system and protocol specifically designed for such plant cells. Such methods of targeted alteration of DNA in a plant cell may, preferably, be successfully applied on various plant cells and with a suitable efficiency in comparison to methods known in the art.

In light of this, new methods for targeted alteration of DNA in plant cells, and for providing plant cells and plants wherein a targeted alteration has been introduced, would be highly desirable. In particular, there is a clear need in the art for reliable, efficient, reproducible and in particular targeted methods that allow for efficient targeted alteration of a DNA molecule in a plant cell. Accordingly, the technical problem underlying the present invention can be seen in the provision of methods for complying with any of the aforementioned needs. The technical problem is solved by the embodiments characterized in the claims and disclosure below.

SUMMARY OF THE INVENTION

In a first aspect, the present disclosure provides a method of targeted alteration of duplex DNA in a plant, wherein the first DNA strand of the duplex DNA comprises a target sequence and the second DNA strand of the duplex DNA comprises a sequence complement to the target sequence, the method comprising:
(a) providing plant cells or plant protoplasts comprising said duplex DNA; and
(b) exposing said duplex DNA in said cells or protoplasts to:
a Cpf1 protein; and
a crRNA comprising a guide sequence for targeting said Cpf1 protein to the site of the duplex DNA comprising the target sequence.

Said duplex DNA may be exposed to said Cpf1 by introducing into the plant protoplast a nucleic acid construct for the transient expression of said Cpf1.

Said duplex DNA may be exposed to said crRNA by introducing into the plant protoplast a nucleic acid construct for transient expression of said crRNA.

In an embodiment, said duplex DNA is exposed to said Cpf1 and crRNA by introducing into the plant protoplast a nucleic acid construct for the transient expression of said Cpf1 and said crRNA.

In an embodiment, the nucleotide sequence encoding said crRNA is operably linked to a polIII promoter.

In an embodiment, said construct for the transient expression of said Cpf1 comprises a nucleotide sequence encoding Cpf1 that is operably linked to a constitutive 35S promoter.

In an embodiment, in step (b) the duplex DNA is exposed to said Cpf1 and crRNA by introduction thereof, or of a nucleic acid construct encoding the same, using polyethylene glycol mediated transformation.

In a preferred embodiment, the nucleotide sequence encoding Cpf1 is codon-optimized for expression in plant cells or plant protoplast.

In an embodiment, the method taught herein further comprises a step of synchronizing the cell cycle phase of the cell or protoplast, preferably before and/or during performing step (b), preferably wherein synchronizing is performed by contacting the cell or protoplast with a synchronizing agent.

In an embodiment, the step of synchronizing the cell phase synchronizes the protoplast in the S-phase, the M-phase, the G1 and/or G2 phase of the cell cycle.

In an embodiment, two or more crRNAs are used.

In an embodiment, at least one targeted alteration is introduced in the duplex DNA, preferably wherein the alteration comprises the insertion, deletion or modification of at least one base pair.

In an embodiment, the alteration comprises the deletion of at least one base pair and the insertion of at least one base pair.

In an embodiment, the at least one targeted alteration is biallelic.

In an embodiment, the method taught herein further comprises the step of regenerating a plant cell or plant from the plant protoplast, wherein the plant cell, plant or progeny thereof comprises the at least one targeted alteration.

Finally, the present disclosure teaches a plant, plant part, seed, or plant cell obtainable by the method taught herein, wherein the plant, plant part, seed, or plant cell is modified compared to a control plant, plant part, seed, or plant cell, and wherein said control plant, plant part, seed, or plant cell is a plant, plant part, seed, or plant cell before the at least one targeted alteration was introduced by the method taught herein.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

The singular terms "a," "an," and "the" include plural referents unless the context clearly dictates otherwise. Thus, for example, reference to "a cell" includes a combination of two or more cells, and the like.

The term "and/or" refers to a situation wherein one or more of the stated cases may occur, alone or in combination with at least one of the stated cases, up to with all of the stated cases.

The term "comprising" is construed as being inclusive and open ended, and not exclusive. Specifically, the term and variations thereof mean the specified features, steps or components are included. These terms are not to be interpreted to exclude the presence of other features, steps or components.

The term "chimeric gene" refers to any gene which is not normally found in nature in a species, in particular a gene in which one or more parts of the nucleic acid sequence are not associated with each other in nature. For example, the promoter is not associated in nature with part or all of the transcribed region or with another regulatory region. The term "chimeric gene" is understood to include expression constructs in which a promoter or transcription regulatory sequence is operably linked to one or more coding sequences.

"Codon-optimized": this term refers to one or more replacement(s) of codon of a nucleic acid from a first organism (for example a bacterium) with codon more frequently used in a second, different, organism (for example a plant), to adapt and optimize (gene) expression in the second organism.

"Construct" or "nucleic acid construct" or "vector": this refers to a man-made nucleic acid molecule resulting from the use of recombinant DNA technology and which is used to deliver exogenous DNA into a host cell, often with the purpose of expression in the host cell of a DNA region comprised on the construct. The vector backbone of a construct may for example be a plasmid into which a (chimeric) gene is integrated or, if a suitable transcription regulatory sequence is already present (for example a (inducible) promoter), only a desired nucleic acid sequence (e.g. a coding sequence) is integrated downstream of the transcription regulatory sequence. Vectors may comprise further genetic elements to facilitate their use in molecular cloning, such as e.g. selectable markers, multiple cloning sites and the like.

"Expression": this refers to the process wherein a DNA region, which is operably linked to appropriate regulatory regions, particularly a promoter, is transcribed into an RNA, which is capable of being translated into a protein or peptide.

"Plant": this includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grains and the like. Non-limiting examples of plants include crop plants and cultivated plants, such as barley, cabbage, canola, cassava, cauliflower, chicory, cotton, cucumber, eggplant, grape, hot pepper, lettuce, maize, melon, oilseed rape, potato, pumpkin, rice, rye, sorghum, squash, sugar cane, sugar beet, sunflower, sweet pepper, tomato (e.g. *Solanum lycopersicum*), water melon, wheat, and zucchini.

"Sequence" or "Nucleic acid sequence": This refers to the order of nucleotides of, or within a nucleic acid. In other words, any order of nucleotides in a nucleic acid may be referred to as a sequence of nucleic acid sequence. Likewise, a "target sequence" is to denote an order of nucleotides within a nucleic acid that is to be targeted, i.e. wherein an alteration is to be introduced. Within the context of the current invention a first nucleic acid sequence may be comprised within or overlap with a further nucleic acid sequence. For example, the targets sequence is an order of nucleotides comprised by a first strand of a DNA duplex.

"Guide sequence" is to be understood herein as the section of the guide RNA (which preferably is a crRNA or sgRNA) which is for targeting the guide RNA to the target sequence.

In the context of formation of a CRISPR complex, the term "target sequence" refers to a sequence to which a guide sequence is designed to target, e.g. have complementarity, where hybridization between a target sequence and a guide sequence promotes the formation of a CRISPR complex. The guide RNA may be sgRNA (e.g. in case of Cas9) comprising a tracrRNA sequence or crRNA (e.g. in case of Cpf1) lacking a tracrRNA sequence. A target sequence may comprise any polynucleotide, such as DNA or RNA polynucleotides and is comprised within a target locus of interest. In some embodiments, a target sequence is located in the nucleus or cytoplasm of a cell. The target sequence may be any DNA or RNA sequence. In some embodiments, the target sequence may be a sequence within a RNA molecule selected from the group consisting of messenger RNA (mRNA), pre-mRNA, ribosomaal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably, the guide sequence is 10-30 or 15-25 nucleotides long.

The term "a nucleic acid-targeting complex" or "CRISPR complex" as used herein refers to a complex of a guide RNA hybridized to a target sequence and complexed with one or more Cpf1 proteins. Formation of a nucleic acid-targeting complex results in cleavage of both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest).

DETAILED DESCRIPTION OF THE INVENTION

In a first aspect, the present disclosure provides a method for targeted alteration of duplex DNA, e.g. at a target locus of interest, in a plant, wherein the first DNA strand of the duplex DNA comprises a target sequence and the second DNA strand of the duplex DNA comprises a sequence complementary to the target sequence, the method comprising the steps of:
(a) providing plant cells or plant protoplasts comprising said duplex DNA; and
(b) exposing said duplex DNA in said protoplasts to
a Cpf1 protein; and
a guide RNA (crRNA) comprising a guide sequence for targeting said Cpf1 to the site of the duplex DNA, e.g., at the target locus of interest, comprising the target sequence.

In an embodiment, the targeted alteration comprises the introduction of a strand break, such as a double-strand break.

The duplex DNA may be present at a target locus of interest. The duplex DNA may be comprised in a DNA molecule within a cell. The cell may be a plant cell, or a plant protoplast. The plant cell or plant protoplast may be of a crop plant such as a monocot or dicot or of a crop or grain plant such as cassava, corn, sorghum, soybean, wheat, oat or rice. The plant cell may also be of an alga, tree or production plant, fruit or vegetable (e.g., trees such as citrus trees, e.g., orange, grapefruit or lemon trees; peach or nectarine trees; apple or pear trees; nut trees such as almond or walnut or pistachio trees; nightshade plants; plants of the genus *Brassica*; plants of the genus *Lactuca*; plants of the genus *Spinacia*; plants of the genus *Capsicum*; plants of the genus *Solanum*; cotton, tobacco, asparagus, carrot, cabbage, broccoli, cauliflower, tomato, eggplant, pepper, lettuce, spinach, strawberry, blueberry, raspberry, blackberry, grape, coffee, cocoa, etc). Preferably, the plant cell is *Solanum lycopersicum* plant cell.

The invention provides a method of modifying a target locus of interest, the method comprising delivering to said locus a non-naturally occurring or engineered composition comprising a Cpf1 protein and one or more nucleic acid components, for example a crRNA, wherein the Cpf1 protein forms a complex with the one or more nucleic acid components and upon binding of the said complex to the locus of interest the Cpf1 protein induces the modification of the target locus of interest. In a preferred embodiment, the modification is the introduction of a double-strand break.

The target locus of interest may be a genomic or epigenomic locus of interest. The complex may be delivered with multiple crRNAs for multiplexed use. More than one Cpf1 protein(s) may be used. Any Cpf1 protein, including orthologues or engineered Cpf1 proteins that recognize different PAM sequences, may be used.

According to the invention, any type of plant cell may be used in the method as long as the plant cells allows the exposure of the DNA duplex to the site-specific nuclease, the single-stranded oligonucleotide and, in some embodiments, the guide RNA (crRNA). However, in a preferred embodiment the plant cell is a plant protoplast. The skilled person is aware of methods and protocols for preparing and propagation plant protoplasts, see for example Plant Tissue Culture (ISBN: 978-0-12-415920-4, Roberta H. Smith). The plant protoplasts for use in the method of the current invention can be provided using common procedures (e.g. using cellulases and pectinase) used for the generation of plant cell protoplasts.

Plant cell protoplasts systems have for example been described for tomato, tobacco and many more (*Brassica napus, Daucus carota, Lactucca sativa, Zea mays, Nicotiana benthamiana, Petunia hybrida, Solanum tuberosum, Oryza sativa*). The present invention is generally applicable to any protoplast system, including those, but not limited to, the systems described in any one of the following references: Barsby et al. 1986, Plant Cell Reports 5(2): 101-103; Fischer et al. 1992, Plant Cell Rep. 11(12): 632-636; Hu et al. 1999, Plant Cell, Tissue and Organ Culture 59: 189-196; Niedz et al. 1985, Plant Science 39: 199-204; Prioli and Sondahl, 1989, Nature Biotechnology 7: 589-594; S. Roest and Gilissen 1989, Acta Bot. Neerl. 38(1): 1-23; Shepard and Totten, 1975, Plant Physiol. 55: 689-694; Shepard and Totten, 1977, Plant Physiol. 60: 313-316, which are incorporated herein by reference.

The Cpf1 protein may be any Cpf1 protein known in the art or yet to be discovered. In an embodiment, the Cpf1 protein may be the Cpf1 protein of *Acidaminococcus* or a Cpf1 protein derived from *Acidaminococcus*. Said *Acidaminococcus* Cpf1 protein or said protein derived from *Acidaminococcus* may be codon-optimized for expression in plants. The skilled person is well-acquainted with methods of codon-optimizing expression of foreign proteins in plants.

In an embodiment, said Cpf1 protein is a protein having an amino acid sequence as shown in FIG. 1, or a variant thereof having at least 70%, such as at least 75%, 80%, 85%, 90%, 95%, 96%, 97%, 98%, or 99% sequence identity to the protein having an amino acid sequence as shown in FIG. 1.

In a preferred embodiment of the method of the invention the duplex DNA is exposed to the Cpf1 protein by introducing into the plant cell a nucleic acid construct for expression of the Cpf1 protein in the plant cell.

The methods of the invention do not depend on a particular method for introducing the Cpf1 protein into the plant cell. In some embodiments, the Cpf1 protein is provided to the plant cells as a polypeptide, the polypeptide being taken up into the plant cell interior.

In other embodiments, the Cpf1 protein is provided by introducing into the plant cell a nucleic acid construct, i.e. a polynucleotide, for expression of the Cpf1 protein in the plant cell. Such nucleic acid construct may be any suitable construct known in the art and which is used to deliver exogenous DNA into a host cell with the purpose of expression in the host cell of a DNA region (here the Cpf1 gene) comprised on the construct.

Introduction of the Cpf1 protein or the nucleic acid construct encoding the same may be accomplished by any method known which permits the successful introduction of the protein or the nucleic acid construct into the plant cells, and which, in case of a nucleic acid construct, results in the expression of the introduced nucleic acid. Methods included but are not limited to such methods as transfection, microinjection, electroporation, nucleofection and lipofection.

The crRNA may also be introduced in the plant cell by any suitable method. For example, crRNA may be provided to the plant cell directly, or, in a preferred embodiment, by introducing into the plant cell a nucleic acid construct for expression of the crRNA in the plant cell.

Such nucleic acid construct may be any suitable construct known in the art and which is used to deliver exogenous DNA into a host cell with the purpose of expression in the host cell of a DNA region (here the crRNA) comprised on the construct.

Introduction of the crRNA or the nucleic acid construct encoding the same, may be accomplished by any method known which permits the successful introduction of the crRNA or the nucleic acid construct into the plant cells, and which, in case of a nucleic acid construct, results in the expression of the introduced crRNA. Methods included but are not limited to such methods as transfection, microinjection, electroporation, nucleofection and lipofection.

Preferably the Cpf1 protein and the crRNA are introduced in the plant cell using a nucleic acid construct for expression of both the Cpf1 protein and the crRNA in the plant cell. In such embodiment, it is however preferred that the nucleic acid sequence encoding the site-Cpf1 protein and the nucleic acid sequence encoding the crRNA are under control of different promoters.

For example, the crRNA may, preferably, be under control of, i.e. operably linked to, a pol III promoter (such as U6 and H1) preferably for expression in plant; RNA pol III promoters, such as U6 and H1, which are commonly used to express these small RNAs (see e.g. Ma et al. Molecular Therapy Nucleic Acids (2014) 3, e161).

For example, the Cpf1 protein may, preferably, be under control of a constitutive promotes, preferably for expression in plant, such as the 35 S promoter (e.g. the 35 S promoted from cauliflower mosaic virus (CaMV; Odell et al. Nature 313:810-812; 1985). Other suitable constitutive promoters include, but are not limited to, the cassava vein mosaic virus (CsVMV) promoter, and the sugarcane bacilliform badnavirus (ScBV) promoter (see e.g. Samac et al. Transgenic Res. 2004 August; 13(4):349-61.) Other constitutive promoters include, for example, the core promoter of the Rsyn7 promoter and other constitutive promoters disclosed in WO 99/43 838 and U.S. Pat. No. 6,072,050; ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); AA6 promoter (WO2007/069894); and the like.

The nucleic acid constructs may also include transcription termination regions. Where transcription termination regions are used, any termination region may be used in the preparation of the nucleic acid constructs.

In a preferred embodiment, the nucleic acid construct is for transient expression. In other words, the expression in the plant material is temporary as a consequence of the non-permanent presence of the nucleic acid construct. Expression may, for instance, be transient when the construct is not integrated into the host genome. For example, Cpf1 protein and crRNA may be transiently provided to a plant cell, followed by a decline in the amount of either or both of the components. Subsequently, the plant cell, progeny of the plant cell, and plants which comprise the plant cell or have been derived from the plant protoplast wherein the duplex DNA has been altered, comprise a reduced amount of either or both of the components used in the method of the invention, or no longer contain one or more of the components.

In conjunction with any of the methods and preferred embodiments as disclosed herein, the nucleic acid construct may be optimized for increased expression in the transformed plant.

In this embodiment, there is provided for the method of the invention, wherein the nucleic acid sequence encoding the Cpf1 protein is codon-optimized for expression in the plant cell. For instance, the nucleic acid sequence encoding the Cpf1 protein may be codon-optimized for expression in tomato, wherein said tomato preferably is *Solanum lycopersicum*.

That is, the nucleic acid construct encoding the Cpf1 protein can be synthesized using plant-preferred codons for improved expression. See, for example, Campbell and Gowri, (Plant Physiol. 92: 1-11, 1990) for a discussion of host-preferred codon usage. Methods are available in the art for synthesizing plant-preferred genes (see, for example, Murray et al., Nucleic Acids Res. (1989) 17:477-498, or Lanza et al. (2014) BMC Systems Biology 8:33-43).

Introduction in the plant cell of the Cpf1 protein, the crRNA, and/or, where applicable, a nucleic acid construct encoding the Cpf1 protein and/or the crRNA, may be accomplished by any method known which permits the successful introduction thereof into the plant cell, and which, in case of a nucleic acid construct, results in the expression of the introduced Cpf1 protein and/or crRNA. Methods included but are not limited to such methods as transfection, microinjection, electroporation, nucleofection and lipofection.

However, in a preferred embodiment, there is provided for a method of the invention wherein in step (b) the duplex DNA is exposed to the Cpf1 protein and the crRNA, by introduction thereof, or of a nucleic acid construct encoding the same, in the plant cell or plant protoplast using polyethylene glycol mediated transformation.

Polyethylene glycol (PEG) is a polyether compound with many applications from industrial manufacturing to medicine. PEG is also known as polyethylene oxide (PEO) or polyoxyethylene (POE). The structure of PEG is commonly expressed as H—(O—CH2-CH2)n-OH. Preferably, the PEG used in the method according to the invention is an oligomer and/or polymers, or mixtures thereof with a molecular mass below 20,000 g/mol. PEG-mediated gene transformation has been known since 1985. The first method for plant protoplast transformation utilized PEG (Krens et al. (1982) Nature 296: 72-74; Potyrykus et al. (1985) Plant Mol. Biol. Rep. 3:117-128; Negrutiu et al. (1987) Plant Mol. Biol. 8: 363-373). The technique is applicable to protoplasts from many different plants (Rasmussen et al. (1993) Plant Sci. 89: 199-207). PEG is thought to stimulate transformation by precipitating the DNA, in the presence of divalent cations, onto the surface of the plant protoplasts from where it then becomes internalized (Maas & Werr (1989) Plant Cell Rep. 8: 148-151). In a preferred embodiment, a solution comprising 400 g/L PEG 4000 and 0.1M $Ca(NO_3)_2$ is used for transformation.

However, hitherto the use of PEG transformation in the method of the invention to introduce into the plant cell or plant protoplast the Cpf1 protein and/or the crRNA, or a nucleic acid construct encoding either or both of the Cpf1 protein and the crRNA has not been proposed.

In an embodiment the weight ratio of Cpf1 protein expressing plasmid relative to crRNA expressing plasmid is in the range of 0.1:20, such as 0.5-10, or 0.75:5, more preferred in the range of 1:3, even more preferred in the range of 1.5:2.5, such as about 1:2.

In an embodiment, at least 0.1 µg of Cpf1 expressing plasmid is used, such as at least 0.5 µg, at least 1 µg, at least 5 µg, or at least 10 µg.

In an embodiment, said at least 0.1 µg, such as at least 0.5 µg, at least 1 µg, at least 5 µg, or at least 10 µg, of Cpf1 expressing plasmid is combined with crRNA expressing plasmid in the appropriate weight range as taught herein, and said combination of Cpf1 expressing plasmid and crRNa expressing plasmid is combined with 10,000-10,000,000, preferably about 50,000-5,000,000, more preferably about 100,000-1,000,000, for example about 500,000 plant cells or plant protoplasts.

In an embodiment, the plant cells or plant protoplasts may be present in a volume of about 500 µl. In an embodiment, the volume ratio of plant cell/plant protoplast (including Cpf1 protein/crRNA) to PEG solution, which is preferably a solution comprising 400 g/L PEG 4000 and 0.1M $Ca(NO_3)_2$, is in the range of 1:0.5 to 1:1.5, and preferably about 1:1.

In an embodiment, PEG transfection may be allowed to take place fora period of time in the range of 10-60 minutes, such as 15-40 minutes, preferably about 20 minutes.

Subsequently, a 0.1-0.6 M, such as a 0.2-0.4 M, or about 0.275 M, $Ca(NO_3)_2$ solution may be added to the transfection solution taught above. Preferably about 8-12 times, such as about 10 times the volume of the transfection solution taught above may be used prior to harvesting by centrifugation.

According to another embodiment, there is provided for a method according to the invention wherein the method comprises a step of synchronizing the cell cycle of the plant cell, preferably before and/or during performing step (b), preferably wherein synchronizing is performed by contacting the plant cell with a synchronizing agent.

Such method of synchronizing the cell cycle of the plant cell has been described in detail in European patent EP2516652, incorporated herein by reference. More particular, synchronizing the plant cells, for example, the plant protoplasts may be advantageous in certain embodiments of the invention to further enhance efficacy of the introduction of the alteration in the duplex DNA. Thus, in certain embodiments, the method comprises a step of synchronizing the cell cycle of the plant cell.

Preferably, synchronization is performed before and/or during performing step (b). In case synchronization is performed before step (b), most of the plant cells will be in the same phase of the cell cycle when the duplex DNA is exposed to, for example, the Cpf1 protein and/or crRNA as defined herein. This may be advantageous and increase the rate of introduction of the alteration in the duplex DNA. Also in case the plant cells are synchronized during step (b), this may increase overall introduction of the alteration in the duplex DNA.

Synchronizing the plant cell may be accomplished by any suitable means. For example, synchronization of the cell cycle may be achieved by nutrient deprivation such as phosphate starvation, nitrate starvation, ion starvation, serum starvation, sucrose starvation, auxin starvation. Synchronization can also be achieved by adding a synchronizing agent to the plant cell.

Synchronizing agents such as aphidocolin, hydroxyurea, thymidine, colchicine, cobtorin, dinitroaniline, benefin, butralin, dinitramine, ethalfluralin, oryzalin, pendimethalin, trifluralin, amiprophos-methyl, butamiphos dithiopyr, thiazopyr propyzamide, tebutam DCPA (chlorthal-dimethyl), mimosine, anisomycin, alpha amanitin, lovastatin, jasmonic acid, abscisic acid, menadione, cryptogeine, hydrogenperoxide, sodiumpermanganate, indomethacin, epoxomycin, lactacystein, icrf 193, olomoucine, roscovitine, bohemine, staurosporine, K252a, okadaic acid, endothal, caffeine, MG 132, cycline dependent kinases and cycline dependent kinase inhibitors as well as their target mechanism, the amounts and concentrations and their associated cell cycle phase are described for instance in "Flow Cytometry with plant cells", J. Dolezel c.s. Eds. Wiley-VCH Verlag 2007 pp 327 ff. There exists a preference for aphidicolin and/or hydroxyurea.

Preferably, in the method of the invention, synchronizing the cell cycle synchronizes the plant cell in the S-phase, the M-phase, the G1 and/or G2 phase of the cell cycle.

According to another preference, in the method of the invention two or more crRNA's are used. The two or more crRNA's may direct the Cpf1 protein to the same site in the DNA duplex, or to a different site (for example in order to introduce more than one double-strand break).

According to another preference the Cpf1 protein and the crRNA are transiently expressed in the plant cell, as already discussed herein above.

With the method taught herein an alteration in introduced in the duplex DNA in a plant protoplast. The targeted alteration may comprise the insertion, deletion or modification of at least one base pair. For example, the targeted alteration may comprise the deletion of at least one base pair and the insertion of at least one base pair. For example, 1, 2, 3, 4, 5, 6, 7, 8, 9, 10 or more base pairs may be altered with the method of the invention. More than one modification may be introduced in a single experiment, and/or the experiment may be repeated to introduce subsequent alterations in the duplex DNA in the plant cell.

According to another embodiment of the present invention, the method further comprises the step of regenerating a plant or descendent thereof comprising the targeted alteration. The skilled person is well aware of methods and protocols of regenerating a plant from a plant protoplast. Progeny, descendant's, variants, and mutants of the regenerated plants are also included within the scope of the invention, provided that these parts comprise the targeted alteration introduced with the method taught herein.

Finally, there is provided for a plant, plant part, seed, or plant cell obtained by the method of the invention, wherein the plant, plant part, seed, or plant cell is modified by comprising the targeted alteration when compared to a control plant, plant part, seed, or plant cell, and wherein the control plant, plant part, seed, or plant cell is a plant, plant part, seed, or plant cell before the targeted alteration was introduced by the method as taught herein.

Having now generally described the invention, the same will be more readily understood through reference to the following examples which is provided by way of illustration and is not intended to be limiting of the present invention.

BRIEF DESCRIPTION OF THE FIGURES

FIGS. 1.1 and 1.2 show the protein sequence of Cpf1-His-NLS, in which the 6×His domain is underlined and the NLS sequence is shown in bold, and the nucleotide sequence of the Cpf1-His-NLS ORF.

FIG. 2 shows the sequences of the crRNAs and sgRNAs used in the examples section. The sequence of the *Arabidopsis thaliana* U6 promoter is underlined. The sequences derived from the target genes are shown in bold and the remainder of the crRNA or sgRNA is shown in italics.

FIG. 4 shows indel mutations generated by the Cpf1/crRNA1 PDS1 and the Cpf1/crRNA2 PDS1 reagents at the tomato PDS1 gene.

EXAMPLES

Example 1

Constructs

Figure 3:
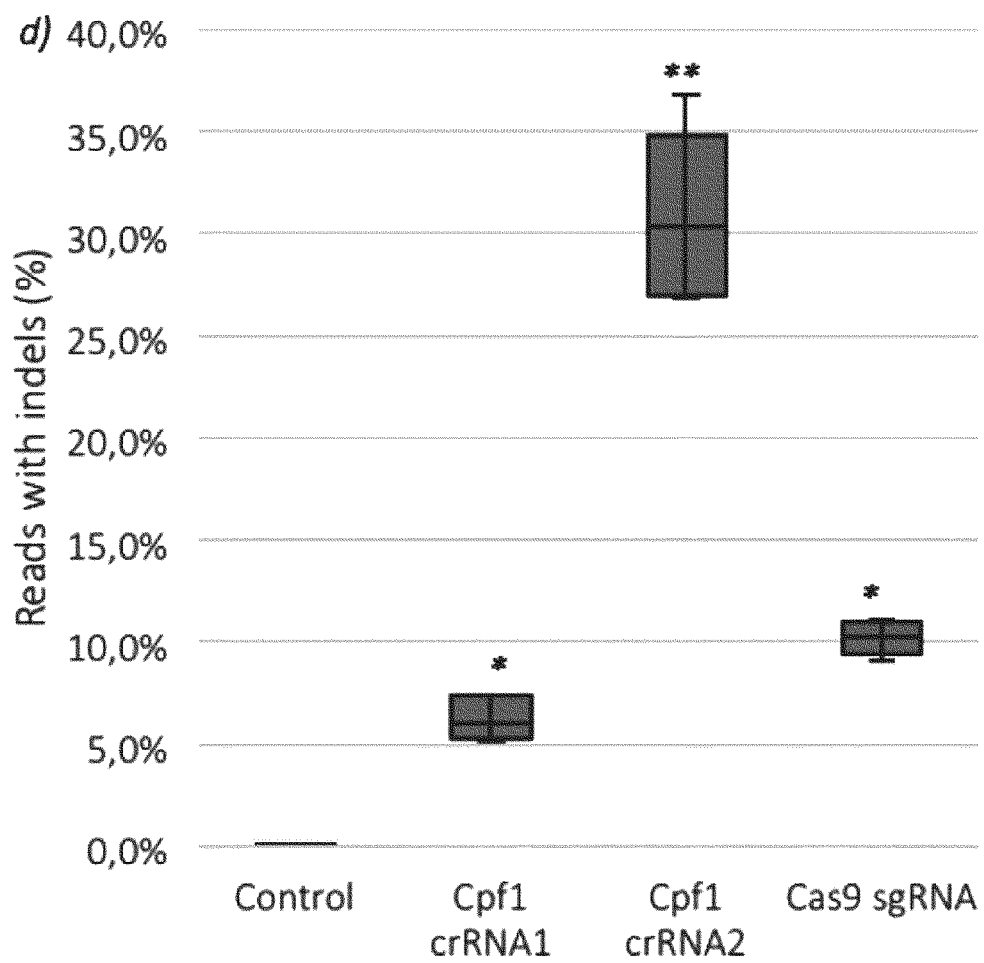
FIG. 3 shows quantification of the indels found in tomato protoplasts treated with either Cpf1 or Cas9. The Cpf1 crRNA1 and Cas9 sgRNA generate indels at the same target sequence whereas the Cpf1 crRNA2 creates indels at an alternative position. Control samples were derived from protoplasts transfected only with the Cpf1 or Cas9 expressing plasmid but not the plasmid expressing the corresponding targeting RNA.

The Cpf1 ORF from the bacterium Acidaminococcus sp BV3L6 was codon optimized for expression in *Solanum lycopersicum* and a NLS and 6×His sequence was added to the C terminus (FIG. 1). This modified Cpf1 ORF was then synthesized (geneart.com) in the Gateway entry vector pDONR221. The Cpf1 ORF was then recombined with the plant expression vector K2GW7 in a Gateway LR reaction resulting in a vector (KG9858) where the Cpf1 ORF is expressed using the constitutive 35S promoter.

We designed four Cpf1 crRNAs (crRNAs) which will target the Cpf1 protein to three different genes in the tomato genome, PDS1, Met1 and Solyc3g095310. In order to compare the mutagenesis frequency of Cpf1 and Cas9 we also designed guide RNAs (sgRNAs) for Cas9 that will target the Cas9 protein to the same location. The crRNAs and sgRNAs were expressed using the U6 polIII promoter from *Arabi-*

*dopsis thaliana*. The expression cassettes used in these experiments are shown in FIG. 2.

Tomato Protoplast Isolation and Transfection

In vitro shoot cultures of *Solanum lycopersicum* var Moneyberg were maintained on MS20 medium with 0.8% agar in high plastic jars at 16/8 h photoperiod of 2000 lux at 25° C. and 60-70% RH. Young leaves (1 g) were gently sliced perpendicularly to the mid nerve to ease the penetration of the enzyme mixture. Sliced leaves were transferred to the enzyme mixture (2% Cellulase Onozuka RS, 0.4% Macerozyme Onozuka R10 in CPW9M) and cell wall digestion was allowed to proceed overnight in the dark at 25° C. The protoplasts were filtered through a 50 μm nylon sieve and were harvested by centrifugation for 5 minutes at 800 rpm. Protoplasts were resuspended in CPW9M (Frearson, 1973) medium and 3 mL CPW18S (Frearson, 1973) was added at the bottom of each tube using a long-neck glass Pasteur pipette. Live protoplasts were harvested by centrifugation for 10 minutes at 800 rpm as the cell fraction at the interface between the sucrose and CPW9M medium. Protoplasts were counted and resuspended in MaMg (Negrutiu, 1987) medium at a final density of $10^6$ per mL.

For the protoplast transfections 10 μg of the Cas9 or Cpf1 expression plasmids and 20 μg of the sgRNA or crRNA expressing plasmids were mixed with 500 μL (500000 protoplasts) of the protoplast suspension and 500 μL of PEG solution (400 g/l poly(ethylene glycol) 4000, Sigma-Aldrich #81240; 0.1M $Ca(NO_3)_2$) was then added and the transfection was allowed to take place for 20 minutes at room temperature. Then, 10 mL of 0.275 M $Ca(NO_3)_2$ solution was added and thoroughly, but gently mixed in. The protoplasts were harvested by centrifugation for 5 minutes at 800 rpm and resuspended in 9M culture medium at a density of $0.5 \times 10^6$ per ml and transferred to a 4 cm diameter petri dish and an equal volume of 2% alginate solution (20 g/l Alginate-Na (Sigma-Aldrich # A0682), 0.14 g/l $CaCl_2.2H_2O$, 90 g/l mannitol) was added. Then 1 ml aliquots (125000 transfected protoplasts) were spread over Ca-Agar plates (72.5 g/l mannitol, 7.35 g/l $CaCl_2.2H_2O$, 8 g/l agar, pH 5.8) and allowed to polymerise for 1 hour. For protoplast cultivation the embedded protoplasts were grown in a 4 cm tissue culture dish containing 4 ml of K8p (Kao, 1975) culture medium. To detect indels in tomato protoplasts the disc of transfected protoplasts was removed from the dish after 48 hours and the alginate was dissolved (which buffer) and the protoplasts were isolated. For the regeneration of calli, the protoplasts were incubated in the K8p medium for 21 days at 28° C. in the dark. After this period the discs of transfected protoplasts were transferred to solid GM medium (Tan, 1987) supplemented with 1 mg·l$^{-1}$ zeatin and 0.2 mg·l$^{-1}$ GA3 and grown for a further 3 weeks at which point the calli were approximately 0.3 mm in size. The aliginate was then dissolved and the calli were spread on a fresh plate of GM medium and allowed to grow until they were approximately 1.5 mm, at which point they were once again transferred to fresh medium and then genotyped after a further 14 days.

Genotyping Protoplasts and Calli

Tomato protoplasts that had been transfected with the Cas9/sgRNA plasmids or the Cpf1/crRNA plasmids were cultivated for 48 hours, the alginate dissolved, and collected by centrifugation. Total genomic DNA (gDNA) was then isolated from each sample using the DNeasy Plant Mini Kit (Qiagen).

This gDNA was then used in a PCR reaction to amplify the target sites. The following primers were used to amplify the different target sites: SlPDS1, 5'-TGTGCAGAAC-CACTCCCT-3' and 5'-TTTAGTTGGGCGCGGAGA-3'; Solycl3g095310, 5'-ATGGGAAGCGGTGAAAGAAAG-3' and 5'-AGGGTCACGATGAAGAGTTGG-3'; SlMET1, 5'-GGACACAAAAAGAACAAACGCA-3' and 5'-5'-TAT-GAACCCGCCCTGAGT-3'. These were then used to generate a library which was then sequenced on the MiSeq sequencer with each sample identified using a unique 5 bp tag. After sequencing the reads of each sample were processed to identify the number and types of indels present in each sample.

Calli were genotyped directly using the direct PCR kit (Phire Plant Direct PCR kit, Thermo Scientific) and the gene specific primers described above. The resulting PCR products were then sequenced to identify which calli contained INDEL mutations at the intended target site. These were then transferred to MS medium supplemented with 2 mg·l$^{-1}$ zeatin and 0.1 mg·l$^{-1}$ IAA media after which regenerated tomato plantlets were rooted on MS medium supplemented with 0.5 mg·l$^{-1}$ IBA before transfer to the greenhouse.

Results

We tested the ability of Cpf1 to generate INDEL mutations in the genome plant cells by expressing the Cpf1 protein and its crRNA ectopically in tomato protoplasts. First a Cpf1 ORF optimized for codon usage in tomato was constructed together with a nuclear localization signal (NLS) fused at the C terminus. This was then cloned behind the constitutive CaMV 35S promoter for expression in plant cells. This vector was then introduced into purified tomato leaf protoplasts together with plasmid expressing a crRNA driven by the *Arabidopsis thaliana* U6 promoter. In such a system the Cpf1 mRNA and the crRNA will be expressed at high levels for a short period, 24-48 hours, at which point the introduced plasmids will become degraded by cellular nucleases and the Cpf1 reagents will disappear from the cell. While they are present they are able to find the specific target site in the genome at create INDEL mutations. The introduced plasmids rarely integrate into the genome and so this approach does not result in transgenic lines. The protoplasts were then cultured for 48 hours and then destroyed and genotyped for the presence of an INDEL at the target site.

We found that the Cpf1 protein, when expressed together with either of the crRNAs targeting the SlPDS1 gene, was able to produce INDEL mutations at a high efficiency in tomato protoplasts (FIG. 3). Each transfection was performed in triplo and the samples were sequenced separately to test the effects of Cpf1 in different biological samples. When the crRNA2 PDS1 was used, 30.7% of the reads contained an INDEL at the target site. In contrast, for crRNA1 PDS1 approximately 6.5% of the sequence reads contained INDELs. This result demonstrates that the Cpf1 protein is very efficient at generating INDELs in plant cells and that the efficiency varies depending on the target sequence. As the sgRNA PDS1 targets the same sequence as crRNA PDS1, this allows us to make a direct comparison between the mutation efficiencies obtained when using either the Cas9 or the Cpf1 protein so that we can assess which works better in plant cells. In the sequence reads generated from the SpCas9/sgRNA PDS1 samples, 10% contained INDELs. This is not significantly different from the efficiency obtained using crRNA1 PDS1 as so we can conclude that 48 hrs after transfection both CRISPR proteins had generated mutations at similar frequencies.

Figure 5A:
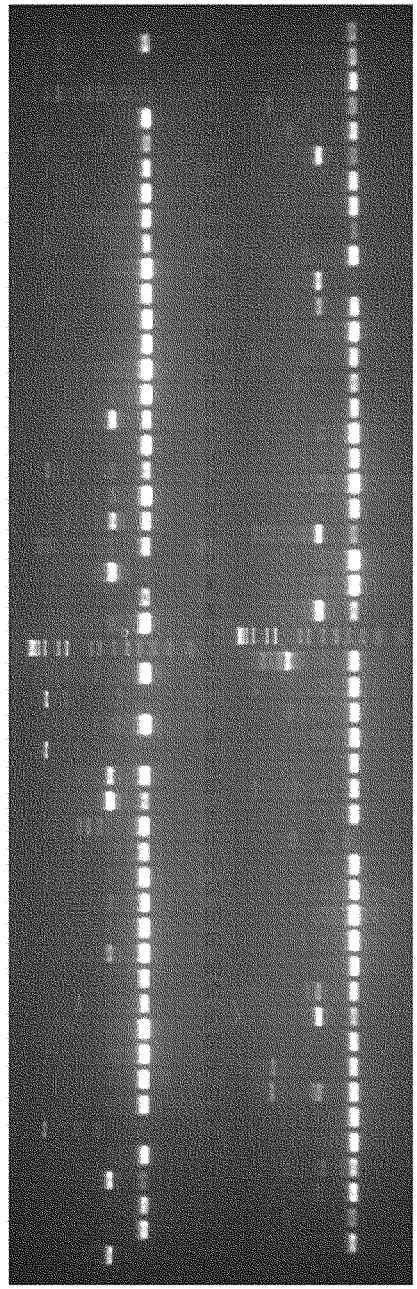
FIGS. 5A and 5B show the genotyping of calli derived from protoplasts treated with Cpf1 protein and crRNA. Panel A: PCR products from calli derived from protoplasts treated with the Cpf1 protein and crRNA1 PDS1 and then digested with the restriction enzyme XhoI. This enzyme cuts in the middle of the PCR product, producing two digestion products of a very similar sizes that are not resolved on an agarose gel. Panel B: PCR products from calli derived from protoplasts treated with the Cpf1 protein and crRNA2 PDS1 and then digested with the restriction enzyme Sau3AI. This enzyme removes a 100 bps fragment from the PCR product.
Figure 5B:
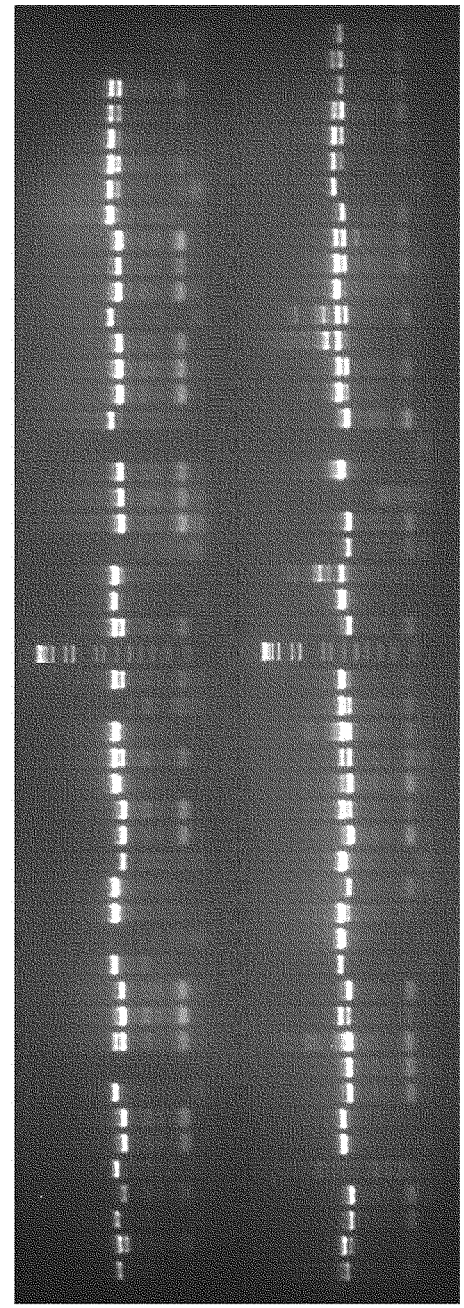

If Cpf1 is to be used to produce novel plants with improved growth and yield characteristics then it is important to demonstrate that plants carrying INDELs at the target sequence can be regenerated from mutated protoplasts. Therefore, we repeated the tomato protoplast transfections described above but in this case maintained the cells in growth medium to promote cell division until the protoplasts had formed calli large enough that could be sampled and genotyped. Each individual callus was sampled by the removal of a small amount of tissue that was used as a template in a direct PCR reaction together with primers designed to amplify the target sites in the PDS1 gene. The Cpf1 target sites both contain a restriction site (XhoI for crRNA1 PDS1 and Sau3A1 for crRNA2 PDS1) which were lost when INDELs were created (FIGS. 3 and 4). Therefore, calli containing INDELs could be easily identified by digesting the PDS1 PCR product with the appropriate restriction enzyme and analysis of these on agarose gels. Calli containing an INDEL mutation gave PCR products that were resistant to restriction enzyme digestion and in this way we were able to easily quantify the mutants. We found that at the crRNA1 PDS1 target, 32% of the calli contained INDELs (FIG. 5), approximately five fold higher than estimated using the sequencing approach. We also found more mutant calli than expected when the crRNA2 PDS1 target was analyzed (FIG. 5). In this case, 57% of the calli contained INDELs at the target. Therefore we were able to conclude that the transient expression of the Cpf1 protein and its crRNA does not negatively influence protoplast growth and that the mutant protoplasts are able to regenerate to form mutant calli. It is very interesting to note that the mutagenesis efficiency in the calli was 2-5 fold higher than we had expected based upon the sequencing results. This is not observed when SpCas9 is used for mutagenesis in tomato protoplasts, where we do not find any significant difference between protoplast and callus efficiencies. One explanation for this may be that the Cpf1 protein and/or its cRNA are more stable in plant protoplasts compared with SpCas9 and/or its sgRNA. As a result of this the Cpf1 protein and crRNA will be active in the plant cells for a longer period and will therefore have a higher likelihood of inducing mutations.

We were also able to quantify the number of calli that contained biallelic mutations at the target sites. Obtaining biallelic mutants can be advantageous as the regenerated plants are usually immediately homozygous for the null alleles and do not have to go through a generation to selfing before they can be analyzed. This is of particular value in crop species that are vegetatively reproduced where mutations cannot be made homozygous. Calli derived from protoplasts transfected with the 35S::Cpf1 and crRNA1 PDS1 vectors showed biallelic mutations at a similar frequency to that found previously using SpCas9 (4/31 mutant calli contained biallelic mutations, 12%). However, we found a much higher percentage of biallelic mutations in calli derived from protoplasts transfected with the 35S::Cpf1 and crRNA2 PDS1 vectors (58/111 mutant calli contained biallelic mutations, 52%). These results demonstrate that Cpf1 is significantly better than SpCas9 for mutagenesis in plant cells. Such a high level of biallelic mutation formation has not previously been reported in plant cells and also represents a significant breakthrough for the mutagenesis of polyploidy crop species. The mutant calli were maintained on growth medium until they regenerated shoots. These were then genotyped to confirm that the mutations present in the callus were also present in the regenerated shoots. We always found the same mutation in the shoots as was originally present in the callus. Therefore, we have been able to show that the Cpf1 CRISPR system can be used to produce mutant plants.

To test whether the Cpf1 CRISPR system was able to generate mutations at other loci in the tomato genome we performed additional similar experiments at target sites in the SlMET1 and Solyc3g095310 loci. For both of these loci we found that the Cpf1 CRISPR system gave significantly higher mutagenesis frequencies than SpCas9. The mutagenesis frequency using Cpf1 was at least two fold higher than when SpCas9 was used. Therefore we conclude that in protoplasts of a polyploid species that the Cpf1 protein, due to its higher mutagenesis efficiency, would be able to introduce INDELs in more of the gene copies and consequently would be more suitable than SpCas9 in producing plants with improved yield and nutritional qualities.

The invention claimed is:

1. A method for producing tomato plant calli, wherein the produced tomato plant calli have a targeted alteration in a target sequence that is comprised within two or more gene copies, the method comprising:
   (a) providing tomato plant protoplasts comprising said target sequence;
   (b) exposing said target sequence in the provided protoplasts to:
      a single RNA-guided endonuclease Cpf1 protein; and
      a crRNA comprising a guide sequence for targeting said Cpf1 protein to the target sequence comprised within the two or more gene copies, by introducing into the tomato plant protoplasts said Cpf1 protein and said crRNA, using polyethylene glycol and divalent cation mediated transformation, resulting in one targeted alteration of the two or more gene copies by said crRNA;
   (c) regenerating calli from said protoplasts obtained in (b);
   (d) genotyping the regenerated calli to detect the targeted alteration of the two or more gene copies; and
   (e) selecting the calli comprising the targeted alteration of the two or more gene copies, wherein the Cpf1 protein comprises an amino acid sequence having at least 99% sequence identity to SEQ ID NO: 7.

2. The method of claim 1, further comprising a step of synchronizing the cell cycle phase of the protoplast, preferably before and/or during performing step (b), preferably wherein synchronizing is performed by contacting the protoplast with a synchronizing agent.

3. The method of claim 2, wherein the step of synchronizing the cell phase synchronizes the protoplast in the S-phase, the M-phase, the G1 and/or G2 phase of the cell cycle.

4. The method of claim 1, wherein the alteration comprises the insertion, deletion or modification of at least one base pair.

5. The method of claim 1, wherein the alteration comprises the deletion of at least one base pair and the insertion of at least one base pair.

6. The method of claim 1, wherein the at least one targeted alteration is biallelic.

7. The method of claim 1, further comprising a step of regenerating a tomato plant from the calli, wherein said tomato plant or progeny thereof comprises the at least one targeted alteration.

8. The method of claim 1, wherein said polyethylene glycol and divalent cation are present in a solution wherein the divalent cation is calcium.

9. The method of claim 8, wherein the polyethylene glycol and calcium are present in a solution wherein the calcium is provided as calcium nitrate.

10. The method of claim 9, wherein the polyethylene glycol and calcium nitrate are present in a solution wherein the concentration of calcium nitrate is 0.1-0.6M.

11. The method of claim 1, wherein the polyethylene glycol is PEG 4000.

12. The method of claim 1, further comprising a step of adding an alginate solution to the protoplasts after transformation.

13. The method of claim 1, wherein the targeted alterations result in null alleles and wherein the selected calli is homozygous for said null alleles.

* * * * *